United States Patent [19]

Hahn et al.

[11] Patent Number: 5,129,889
[45] Date of Patent: Jul. 14, 1992

[54] SYNTHETIC ABSORBABLE EPIDURAL CATHETER

[76] Inventors: John L. Hahn, P.O. Box 248, Petersburg, W. Va. 26847; Philip A. Pappas, 10 Cavalier Dr., Huntington, W. Va. 25701

[21] Appl. No.: 542,883

[22] Filed: Jun. 25, 1990

Related U.S. Application Data

[63] Continuation-in-part of Ser. No. 286,781, Dec. 20, 1988, abandoned, which is a continuation-in-part of Ser. No. 116,162, Nov. 3, 1987, abandoned.

[51] Int. Cl.$^5$ ............................................. A61M 5/32
[52] U.S. Cl. ................................... 604/265; 604/51; 604/158; 604/280
[58] Field of Search ............... 604/51, 264, 265, 272, 604/158, 280; 606/230

[56] References Cited

U.S. PATENT DOCUMENTS

| | | | |
|---|---|---|---|
| 2,593,980 | 4/1952 | Calicchio | 128/350 |
| 4,052,988 | 10/1977 | Doddi et al. | 128/335.5 |
| 4,643,191 | 2/1987 | Bezwada et al. | 606/230 |
| 4,653,497 | 3/1987 | Bezwada et al. | 606/230 |
| 4,700,704 | 10/1987 | Jamiolkowski et al. | 606/230 |
| 4,737,146 | 4/1988 | Amaki et al. | 604/51 |
| 4,994,036 | 2/1991 | Biscoping et al. | 604/158 |
| 5,004,456 | 4/1991 | Botterbusch et al. | 604/53 |

Primary Examiner—C. Fred Rosenbaum
Assistant Examiner—C. Maglione
Attorney, Agent, or Firm—Richard C. Litman

[57] ABSTRACT

A sterile catheter formed of a biodegradable, biocompatible material for use in a continuous epidural anesthesia procedure. The epidural catheter has an effective lumen size and includes a flexible tube molded from a synthetic polymer which is absorbable in living tissue. The catheter is characterized as being dimensionally and structurally stable within the body for the duration of surgery and into the postoperative period and absorbable without causing any unfavorable tissue reaction.

18 Claims, 1 Drawing Sheet

SYNTHETIC ABSORBABLE EPIDURAL CATHETER

CROSS-REFERENCE TO RELATED APPLICATION

This application is a continuation-in-part of application Ser. No. 286,781 filed Dec. 20, 1988, now abandoned, which is a continuation-in-part of application Ser. No. 116,162 filed Nov. 3, 1987, now abandoned.

BACKGROUND OF THE INVENTION

1. Field of the Invention

The present invention relates to epidural catheters and, more particularly, to biocompatible, biodegradable epidural catheters suitable for use in a continuous epidural anethesia procedure comprising a synthetic absorbable polymer.

2. Description of the Prior Art

Epidural blockade has become popular among anesthesiologists and surgeons since it does not entail the risks associated with general anesthesis and can be used to provide complete anesthesia during a prolonged surgical operation. The epidural procedure involves the administration of an anesthetic agent in sufficient dosage into the epidural space to affect all modalities of nerve function, including sensory, motor, and autonomic impulses. To provide a continuous epidural block for the duration of surgery and, if required, into the postoperative period, a flexible, plastic epidural catheter is normally introduced so that repeated or continual injections of an anesthetic agent can be made.

While the insertion of the catheter during the epidural procedure is usually safe, conventional epidural catheters manufactured from non-irritating, flexible plastic materials such as polymers of tetrafluoroethylene, have been knoen to break during removal, leaving a segment lodged in the patient's back. Due to the increased risk to the patient, surgical removal of a broken catheter is not recommended and since the severed nonbiodegradable catheter is located in an anatomical region which does not permit it to be naturally extruded, it must be left in the patient permanently. In any event, the discomfort to the patient and the formidable complications that may likely result from such a mishap following or during the epidural anesthesia procedure could greatly deter surgeons, anesthetists and patients from this most useful anesthetic technique.

To avoid the disadvantages associated with nonbiodegradable delivery systems, a number of biodegradable materials have been used or proposed in the prior art for the manufacture of medical devices based upon ingestion, injection, vaginal and uterine insertion, percutaneous application and subcutaneous implantation. Such absorbable materials as natural collagens, commonly known as catgut, hydrogels, gelatin, methyl cellulose, and polyvinyl alcohol derivatives have traditionally been suggested for these purposes as described in U.S. Pat. Nos. 2,072,303, 2,593,980 and 3,358,684. However, those materials, such as methyl cellulose and polyvinyl alcohol, which are water-soluble are unsatisfactory for use as epidural catheters because it is not possible to control their rate of absorption by living tissue over any appreciable length of time and, therefore, these materials become dimensionally unstable in the body. Also, those materials, such as hydrogels, gelatin and collagens, which are water-swellable do not maintain their structural integrity within the body and there appears to be no satisfactory continuous method for fabricating these materials into fine tubes which would facilitate their use as epidural catheters. Moreover, the absorption process of a natural collagenous material takes place in the body through enzymatic degradation which may result in adverse cellular infiltration and irritation.

More recently, it has been proposed to manufacture sutures, prosthetic devices, implantable drug delivery systems, surgical drainage or testing tubes and tubular structures having use in the surgical repair of arteries, veins and the like from synthetic absorbable polymers such as polylactide, polyglycolide, copolymers of lactide and glycolide, and polydioxanone. Such polymeric articles are described in U.S. Pat. Nos. 3,297,033; 3,463,158; 3,636,956; 3,736,646; 4,052,988; 4,650,488; 4,697,575; 4,706,652 and elsewhere in the literature. However, none of these references suggest a biodegradable catheter made of synthetic polymers of absorbable materials for use in an epidural anesthesia procedure in accordance with a primary object of the present invention.

SUMMARY OF THE INVENTION

It is, accordingly, a primary object of the present invention to provide an epidural catheter having biodegradable and biocompatible properties not available with conventional epidural catheters.

It is a further object of the present invention to provide an improved epidural catheter which is dimensionally and structurally stable within the body over an appreciable length of time and which does not cause any significantly unfavorable tissue reactions upon absorption.

It is among the further objects of the present invention to provide an improved epidural catheter suitable for use in an epidural anesthesia procedure which maintains its structural integrity for the duration of surgery and into the postoperative period; which eliminates the necessity for an additional surgical procedure or any outside intervention in order to remove a portion of the catheter should breakage occur; and which exhibits good handling properties, has adequate tensile strength, is sterilizable and can be uniformly manufactured using conventional techniques.

These and other objects are accomplished in accordance with the present invention which provides a sterile epidural catheter comprised of an absorbable synthetic polymer. The synthetic absorbable epidural catheters of the present invention are formed of a biocompatible, biodegradable polymeric material, e.g., a material that dissolves with time upon contact with moisture found in body fluids and which introduces no undesirable degradation substances into the body. Compounds which may be found to be suitable for this purpose include polymers of dioxanone, caprolactone, glycolide and lactide; copolymers of glycolide and lactide; and copolymers of caprolactone and lactide or glycolide. It is believed that other biodegradable materials such as the synthetic polymer composed of amino acid residues linked by peptide bonds described in U.S. Pat. No. 4,351,337 could also be used.

All or part of the epidural catheter can be formed of such biodegradable material. The portion of the catheter which extends external of the patient's body does not have to be formed of a biodegradable material, but can be if manufacturing techniques make such a structure advantageous. The synthetic absorbable epidural catheters of the present invention can be fabricated into the desired configuration by injection-molding, by melt-extrusion or by other standard techniques. Also, the catheters may be formed by extrusion into a tubular configuration, cutting the extended tube into suitable lengths and forming the desired aperture in the leading end of the tube. Alternatively, the catheters may be molded or formed upon a suitable mandrel.

The degradation rate of the biodegradable material from which the epidural catheter of the present invention is formed can be adjusted to dissolve in various time periods, but in general the material should generally maintain its original integrity for at least three days. The degradation time of the biodegradable material can be selectively altered by adjusting the molecular weight or chemical make-up of the synthetic polymers, or through irradiation with gamma rays which simultaneously sterilizes the catheter without any significant loss of other desirable properties.

Such absorbable catheters have the advantage of being removable without requiring additional surgical intervention following an epidural procedure, but still effectively perform the same function as existing epidural catheters.

The foregoing and other features, advantages and objects of the invention may be more fully appreciated by reference to the following description.

DETAILED DESCRIPTION OF THE PREFERRED EMBODIMENTS

Figure 1:
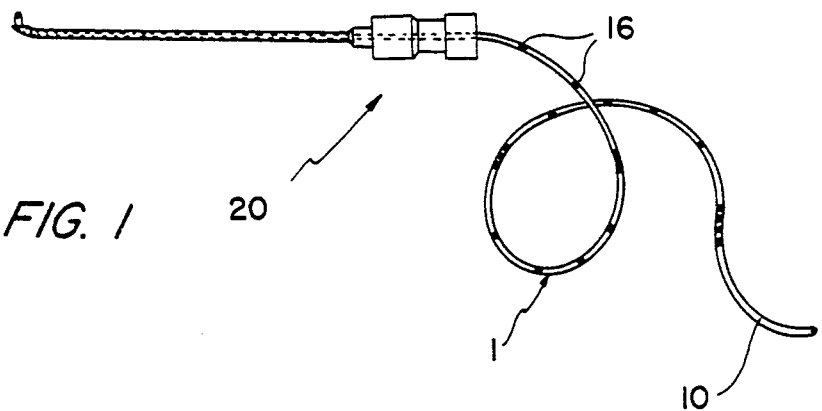
FIG. 1 is a perspective view of a needle-catheter combination.

The preferred embodiments of the epidural catheter for use in continuous epidural anesthesia taught by the present invention are described in detail in conjunction with the drawings. Referring particularly to FIG. 1, an epidural catheter designated generally as reference numeral 1 comprises a section of thin-walled flexible elongated tube 10. The tube 10, which is substantially circular in cross section and molded from synthetic polymers of absorbable materials, possesses an outer diameter determined such that it can smoothly pass through an epidural needle 20. The inner diameter of tube 10 primarily depends upon the volume of an anesthetic solution required and the rate of injecting the anesthetic solution. From a practical standpoint, there is a certain limit for the size of the epidural needle 20 since the pain caused by inserting the epidural needle 20 into the patient should be minimized. Thus, the size of the epidural needle 20 is automatically fixed in a certain range, generally between 15 and 18 gauge, and preferably 17 gauge. Considering that a 17-gauge needle has an inner diameter of about 1.17 mm and an anesthetic solution is generally injected at a rate of about 10 ml/min. (a variation in injection rate can easily be appreciated by one skilled in the art), it is desired that the size of tube 10 be in a range of about 0.6 to about 1.0 mm, preferably 0.8 mm as an inner diameter thereof and 1.0 mm as an outer diameter. The size relation between tube 10 and existing plastic epidural catheters is substantially identical and the epidural catheters of the present invention afford a regional anesthesia as effectively as those conventionally employed in the art.

The flexible tube 10 is formed of synthetic polymers of absorbable materials. Examples of suitable synthetic absorbable materials that may be used to produce the epidural catheters of the present invention are homopolymers of cyclic monomers, such as dioxanone and caprolactone; polylactide; polyglycolide; copolymers of glycolide and lactide; copolymers of a cyclic monomer, such as caprolactone and glycolide or lactide and the like. Such polymeric materials are more fully described in U.S. Pat. Nos. 3,565,869; 3,636,956; 3,736,646; 4,052,988; and 4,650,488, the teachings of which are incorporated herein by reference. Specific examples of such polymers are sold by ETHICON, Inc., Somerville, N.J. under the trademarks "VICRYL" and "PDS"; "PCL-700", a polycaprolactone, is commercially available from Union Carbide Corporation, and "MAXON" is available from American Cyanamid Company, Stamford, Conn.

The absorbable polymers may be melt-extruded continuously into fine tubes using conventional injection-molding techniques and the resulting diameters can be readily changed by switching extrusion dies. Preferably the fabricated tubular polymers should maintain their integrity for at least three days and should be completely absorbed in living tissue in a period of time from about 20 to 120 days. As common with biological systems, the short-term integrity requirement as well as the rate of absorption varies from patient to patient and with the thickness or molecular weight of the polymer. Moreover, a wide range of absorption rates and molecular weights are useful since these properties can be readily adjusted to meet different purposes, either by irradiation or making adjustments in the chemical composition of the polymeric material. Thus, the irradiation process may be used to reduce the molecular weight of an already fabricated higher molecular weight polymer in order to effectuate faster degradation. Irradiation simultaneously results in the sterilization of the absorbable polymeric material, which can also be sterilized by exposure to heat or sterilizing agents such as gamma rays, ethylene oxide gas, cobalt 60, and the like without any significant loss of properties. Further, there is a direct correlation between biodegradation rates and copolymer composition, and by varying the ratio of copolymer components one skilled in the art may directly affect the rate of absorption of the synthetic material. For instance, the prior art shows that in polymers prepared containing lactide with various proportion of glycolide, those having the greater percentage of glycolide exhibit the faster rate of absorption. It is further preferred that the extruded absorbable polymers be transparent, since any undesirable back current of blood which might occur during anesthesia using the epidural catheter in accordance with the present invention can easily be detected with the naked eye.

Figure 2:
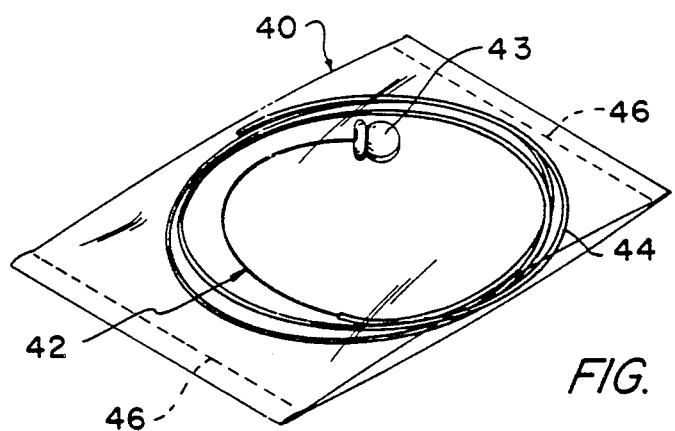
FIG. 2 is a perspective view of a catheter-stylet combination within a sealed container.

While the epidural catheter of this invention is described with reference to its properties, several different structural designs are contemplated. Besides single-lumen type catheters having a single terminal opening, others having up to three lateral holes are also within the scope of this invention. The absorbable epidural catheters may also display appropriate (5 cm) distant markings 16 and be supplied with a stylet 12 as shown in FIG. 2. All are provided with a means of connecting one end of the epidural catheter to a syringe.

The synthetic absorbable epidural catheter 1 having the single-lumen type structure described hereinabove is employed in a method for continuous epidural anesthesia. An anesthetic solution is injected using a syringe (not shown) from the proximal end of the catheter, while detaining the opposite, distal end in the epidural space 37.

Figure 3:
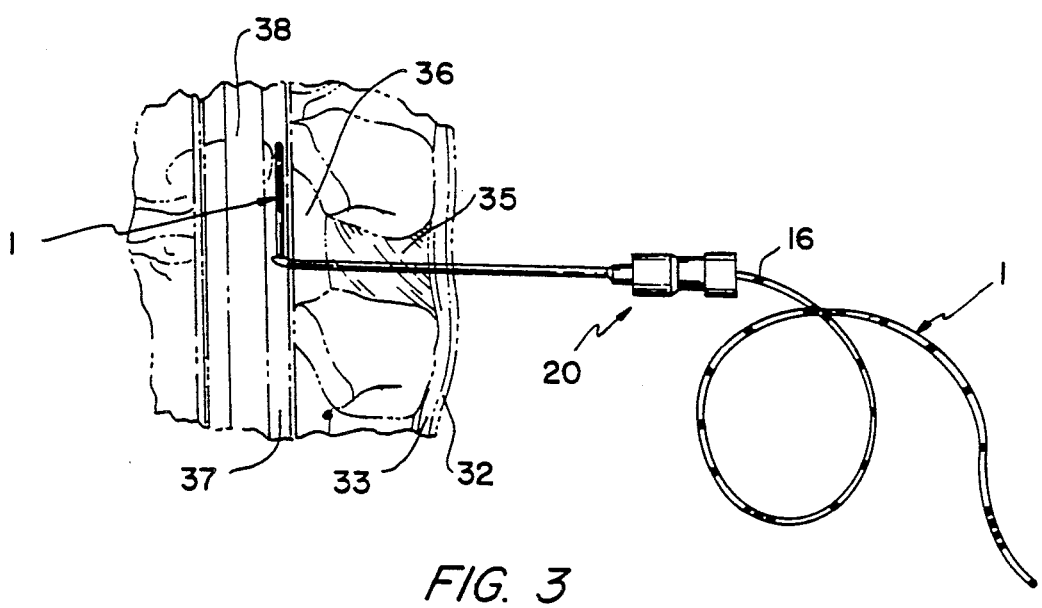
FIG. 3 illustrates the epidural catheter according to the present invention in use.

In more detail, FIG. 3 is a diagrammatic sectional view of the patient's body showing the needle tip as positioned in the epidural space of the patient. The epidural needle 20 is successively introduced through the patient's skin 32 and is slowly and gradually advanced through the subcutaneous tissue 33 until it is firmly engaged in the interspinous ligament 35. The tip of the needle now has to penetrate the ligamentum flavum 36 to reach the epidural space 37. Care should be taken that the needle is pushed through the ligamentum flavum 36 slowly and without a sudden forward movement to avoid penetration of the dura mater 38. The epidural placement of the needle 20 may be detected by various testing methods well-known in the art. The commonest method used is the loss of resistance technique which involves the use of tacile sense with syringes or other mechanical aids which register the slightly negative body pressure of the potential epidural space. During this time, an internal stylet (not shown) may be used in conjunction with needle 20 to prevent coring of body tissue as the needle is being properly positioned in the patient. After epidural placement of the needle 20 has been confirmed, the stylet, if used, is removed from the needle and the synthetic absorbable epidural catheter 1 having a single lumen is then inserted through the needle so that it emerges into the epidural space 37. A slight resistance is felt as the catheter passes through the tip of the needle and about 3-5 cm of catheter is advanced into the epidural space, generally indicated when the appropriate distance mark 16 is at or near the needle hub. Thereafter, the needle 20 is withdrawn carefully without removing the catheter and then completely removed from the patient. Epidural anesthesia is then carried out in the normal way by injection of an anesthetic agent via the absorbable catheter. Should a catheter of the present invention break during removal, leaving a segment in the patient, there is no need to attempt to remove it, given the biocompatible and biodegradable properties of the synthetic material employed.

The catheters of the present invention may also be provided with a stylet which serves as a rigidizing element and is removed from the catheter once it is introduced into the patient's body sufficiently. The rigidity or flexibility of the absorbable catheter is preferably controlled, however, by selection of the synthetic polymeric material employed and the wall dimension or lumen diameter of the catheter used.

The epidural catheters of the present invention are adversely affected by moisture and are accordingly preferably packaged in a substantially moisture-free environment prior to use and in sealed sterile packages, a preferred form of which is shown in FIG. 2. In FIG. 2, there is shown a catheter-stylet package 40 having disposed therein a coil of catheter 44 having an internal stylet 42, one end of which is securely attached to handle 43. The package is fabricated of a transparent plastic material that is evacuated and sealed along the edges 46 to isolate the contents fo the package from the external atmosphere. The catheter may also be included in a sterile epidural pack which may contain the standard Tuohy needle, syringes and other instruments, depending on the personal preference of the anesthetist.

It is preferred that the epidural catheters of the present invention be transparent to permit observation of fluid or, more particularly, blood passage if the catheter should penetrate a vein wall. Intravenous placement can be visually checked before injection of large quantities of local anesthetic and if bloodstained fluid is seen, the catheter must be removed and reinserted. Also, the leakage of cerebrospinal fluid (CSF) into the epidural space may be visually detected by the transparent catheters of the present invention and a continuous infusion of saline solution can be made to raise the epidural pressure and prevent escape of CSF. Occasionally it will be found impossible to inject down a a catheter. This is due either to kinking or to a clot forming in the catheter. The former will usually respond to a change in the patient's position or withdrawal of 1 cm or so of catheter. If the obstruction is due to a clot, the insertion of a stylet may be the solution.

The list of complications associated with a continuous epidural anesthesia procedure, including catheter breakage, may appear to be formidable and could deter from this most useful technique. However, these mishaps are readily overcome by the absorbable epidural catheters provided in accordance with this invention which additionally provide inestimable advantages in ensuring patient safety.

While the invention has been described in detail and with reference to specific embodiments thereof, it will be apparent to one skilled in the art that various changes and modifications can be made therein without departing from the spirit and scope thereof.

We claim:

1. A sterile epidural catheter for use in an epidural anesthesia procedure comprising a biocompatible, biodegradable synthetic polymer absorbable in living tissue, said synthetic polymer being selected from the group consisting of a homopolymer of dioxanone, a homopolymer of caprolactone, polylactide, polyglycolide, a copolymer of lactide and glycolide, a copolymer of caprolactone and glycolide, and a copolymer of caprolactone and lactide, wherein said epidural catheter is substantially circular in cross section having an outer diameter in the range of about 0.6 to about 1.0 mm.

2. The epidural catheter according to claim 1 wherein the catheter has an inner diameter of about 0.8 mm and an outer diameter of about 1.0 mm.

3. The epidural catheter according to claim 1 wherein the absorbable synthetic polymer comprises a copolymer of lactide and glycolide.

4. The epidural catheter according to claim 1 wherein the absorbable synthetic polymer comprises a copolymer of caprolactone and glycolide.

5. The epidural catheter according to claim 1 wherein the absorbable synthetic polymer comprises a copolymer of caprolactone and lactide.

6. The epidural catheter according to claim 1 wherein the absorbable synthetic polymer comprises a homopolymer of dioxanone.

7. The epidural catheter according to claim 1 wherein the catheter comprises a single-lumen type tubular structure having a single terminal opening.

8. The epidural catheter according to claim 7 wherein the catheter is provided with an internal stylet.

9. The epidural catheter according to claim 8 wherein the catheter and stylet combination is packaged in a sterile and dry environment within a sealed and substantially moisture-impervious container.

10. A method for continuous epidural anesthesia, comprising the steps of:
   inserting a rigid, hollow epidural needle successively through a patient's skin, subcutaneous tissue, interspinous ligament and ligamentum flavum until the tip of the needle reaches an epidural space;
   introducing a sterile epidural catheter through the needle, out through an opening in the tip of the needle, and into the epidural space to a length of about 3-5 cm; and
   injecting an anesthetic agent via the epidural catheter, wherein said epidural catheter comprises a biocompatible, biodegradable synthetic polymer absorbable in living tissue selected from the group consisting of a homopolymer of dioxanone, a homopolymer of caprolactone, polylactide, polyglycolide, a copolymer of lactide and glycolide, a copolymer of caprolactone and glycolide, and a copolymer of caprolactone and lactide.

11. The method according to claim 10 wherein said epidural catheter is substantially circular in cross section having an outer diameter in the range of about 0.6 to about 1.0 mm.

12. The method according to claim 11 wherein said epidural catheter has an inner diameter of about 0.8 mm and an outer diameter of about 1.0 mm.

13. The method according to claim 10 wherein the absorbable synthetic polymer comprises a copolymer of lactide and glycolide.

14. The method according to claim 10 wherein the absorbable synthetic polymer comprises a copolymer of caprolactone and glycolide.

15. The method according to claim 10 wherein the absorbable synthetic polymer comprises a copolymer of caprolactone and lactide.

16. The method according to claim 10 wherein the absorbable synthetic polymer comprises a homopolymer of dioxanone.

17. The method according to claim 10 wherein said epidural catheter comprises a single-lumen type tubular structure having a single terminal opening.

18. The method according to claim 17 wherein said epidural catheter is provided with an internal stylet which is removed once said catheter is sufficiently introduced into the patient's body.

* * * * *